United States Patent
Stasi et al.

(10) Patent No.: US 9,498,478 B2
(45) Date of Patent: Nov. 22, 2016

(54) SPIRO AMINIC COMPOUNDS WITH NK1 ANTAGONIST ACTIVITY

(71) Applicant: Rottapharm Biotech Srl, Monza (IT)

(72) Inventors: Luigi Piero Stasi, Monza (IT); Lucio Rovati, Monza (IT)

(73) Assignee: Rottapharm Biotech S.r.l., Monza (IT)

( * ) Notice: Subject to any disclaimer, the term of this patent is extended or adjusted under 35 U.S.C. 154(b) by 0 days.

(21) Appl. No.: 14/922,212

(22) Filed: Oct. 26, 2015

(65) Prior Publication Data

US 2016/0045500 A1 Feb. 18, 2016

Related U.S. Application Data

(62) Division of application No. 13/982,035, filed as application No. PCT/EP2012/051661 on Feb. 1, 2012, now abandoned.

(30) Foreign Application Priority Data

Feb. 2, 2011 (EP) .................................... 11153047

(51) Int. Cl.
| | |
|---|---|
| *A61K 31/506* | (2006.01) |
| *A61K 31/444* | (2006.01) |
| *C07D 401/12* | (2006.01) |
| *C07D 401/14* | (2006.01) |

(52) U.S. Cl.
CPC ........... *A61K 31/506* (2013.01); *A61K 31/444* (2013.01); *C07D 401/12* (2013.01); *C07D 401/14* (2013.01)

(58) Field of Classification Search
CPC ........................... C07D 401/14; C07D 401/12
USPC .......................................... 514/256; 544/230
See application file for complete search history.

(56) References Cited

U.S. PATENT DOCUMENTS 8,859,608 B2 10/2014 Stasi et al.

FOREIGN PATENT DOCUMENTS

| EP | 1057827 A1 | 12/2000 |
|---|---|---|
| WO | 2009133135 A1 | 11/2009 |
| WO | 2010012619 A1 | 2/2010 |
| WO | 2011006960 A1 | 1/2011 |

OTHER PUBLICATIONS

International Search Report for corresponding PCT/EP2012/051661 (Apr. 26, 2012).
Duffy, "Potential Therapeutic Targets for Neurokinin-1 Receptor Antagonists," Expert Opin. Emerg. Drugs 9(1):9-21 (2004).
Munoz et al., "NK-1 Receptor Antagonists: A New Paradigm in Pharmacological Therapy," Current Medicinal Chemistry 18:1820-1831 (2011).

*Primary Examiner* — Rita Desai
(74) *Attorney, Agent, or Firm* — LeClairRyan, a Professional Corporation

(57) ABSTRACT

The invention concerns a spiro-amino compound of Formula (I), wherein A is selected from a 5- or 6-membered aromatic ring and a 5- or 6-membered heteroaromatic ring containing 1 to 3 nitrogen atom; X is a substituent selected from the group consisting of $(C_1-C_3)$alkyl and halogen, Y is a substituent selected from the group consisting of halogen and trifluoromethyl or a pharmaceutically acceptable salt thereof for use in the treatment of pathologies which require an antagonist of the NK1 receptor.

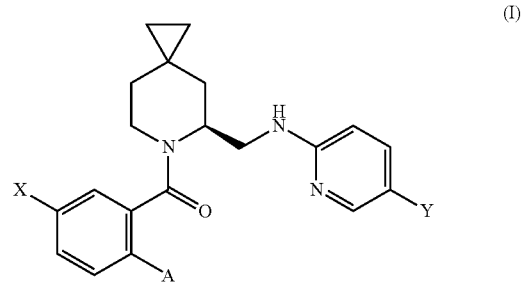

6 Claims, No Drawings

SPIRO AMINIC COMPOUNDS WITH NK1 ANTAGONIST ACTIVITY

This application is a division of U.S. patent application Ser. No. 13/982,035, filed Jul. 26, 2013, which is a national stage application under 35 U.S.C. §371 of PCT International Application No. PCT/EP2012/051661, filed Feb. 1, 2012, which claims priority benefit of European Patent Application No. 11153047.3, filed Feb. 2, 2011, which are hereby incorporated by reference in their entirety.

FIELD OF THE INVENTION

The invention relates to spiro aminic compounds and their pharmaceutically acceptable salts having affinity for and being specific antagonists of the tachykinin NK1 receptor.

The invention also concerns a new compound, i.e. (S)-(5-chloro-2-(pyrimidin-2-yl)phenyl)(5-(((5-chloropyridin-2-yl)amino)methyl)-6-azaspiro[2.5]octan-6-yl)methanone, pharmaceutical compositions containing this compound and its use as antagonists of the NK1 receptor.

BACKGROUND OF THE INVENTION

Tachykinins are a family of peptides that share a common carboxyl-terminal sequence (Phe-X-Gly-Leu-Met-NH2). They are actively involved in the physiology of both lower and advanced life forms. In mammalian life forms, the main tachykinins are substance P (SP), Neurokinin A (NKA) and Neurokinin B (NKB) which act as neurotransmitters and neuromodulators. Mammalian tachykinins may contribute to the pathophysiology of a number of human diseases.

Three types of tachykinins receptors have been identified, namely NK1 (SP-preferring), NK2 (NKA-preferring) and NK3 (NKB-preferring), which are widely distributed throughout the central nervous (CNS) and peripheral nervous system. In the international patent application WO2006/094948 diaza-spiro-[4.4]-nonane derivatives have been disclosed as a series of Neurokinin (NK1) antagonists. Bridged ring NK1 antagonists have been described in the international patent application WO2006/065654.

Novel spiro aminic compounds and their pharmaceutical salts have been disclosed in WO2011/006960, for use in the treatment of pathologies where an antagonist of the OX1 receptor is needed, such as the treatment of obesity, sleep disorders, compulsive disorders, drug dependency, schizophrenia.

The object of the present invention is to provide compounds with antagonist activity of the tachykinin NK1 receptor.

SUMMARY OF THE INVENTION

The object of the invention has been achieved by a spiro-amino compound of Formula (I):

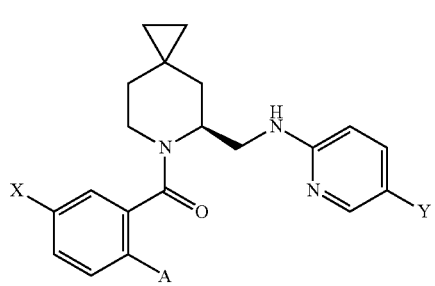

(I)

wherein
A is selected from a 5- or 6-membered aromatic ring and a 5- or 6-membered heteroaromatic ring containing 1 to 3 nitrogen atom:
X is a substituent selected from the group consisting of $(C_1-C_3)$alkyl and halogen,
Y is a substituent selected from the group consisting of halogen and trifluoromethyl
or a pharmaceutically acceptable salt thereof for use in the treatment of pathologies which require an antagonist of NK1 receptor.

In this invention compounds of Formula (I) are S enantiomers.

A further aspect of this invention concerns a novel compound of formula (II):

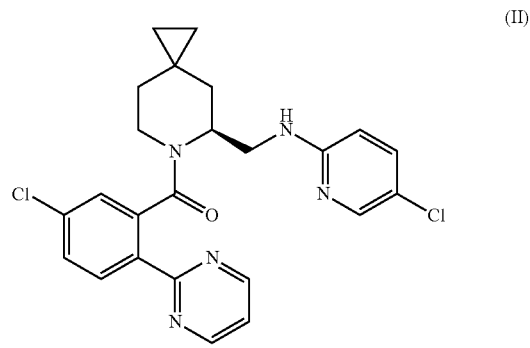 [SMILES: O=C(c1cc(Cl)ccc1-c1ncccn1)N1CCC2(CC2)C[C@H]1CNc1ccc(Cl)cn1]

(II)

or a pharmaceutically acceptable salt thereof.

In another aspect the invention concerns a pharmaceutical composition comprising a compound of Formula (II) and a pharmaceutically acceptable carrier.

In a still further aspect the invention concerns a compound of Formula (II) as a medicament, in particular it concerns the compound of Formula (II) or a pharmaceutically acceptable salt thereof for use as in the treatment of pathologies which require an antagonist of the NK1 receptor.

Particularly, the invention concerns a compound of Formula (I) or (II) for use in the treatment of emesis, depression, eating disorders, pain, gastrointestinal disorders, inflammatory diseases, allergic disorders.

DETAILED DESCRIPTION OF THE INVENTION

The invention thus concerns a spiro-amino compound of Formula (I):

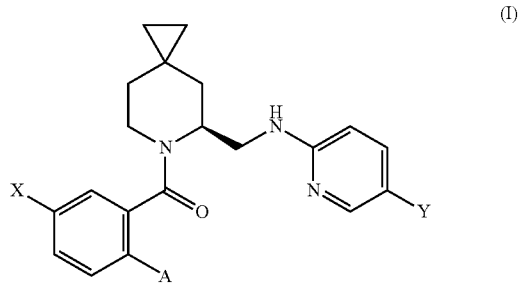

(I)

wherein
A is selected from a 5- or 6-membered aromatic ring and a 5- or 6-membered heteroaromatic ring containing 1 to 3 nitrogen atom:
X is a substituent selected from the group consisting of ($C_1$-$C_3$)alkyl and halogen,
Y is a substituent selected from the group consisting of halogen and trifluoromethyl
or a pharmaceutically acceptable salt thereof for use in the treatment of pathologies which require an antagonist of the NK1 receptor.

Preferably, A is selected from the group consisting of pyrimidinyl, pyridinyl and triazolyl, more preferably pyrimidinyl.

Preferably X is chloro, fluoro or methyl, more preferably methyl.

Preferably Y is chloro or trifluoromethyl, more preferably chloro.

In this invention compounds of Formula (I) are S enantiomers.

The preferred compounds in the use of the invention are selected from the group consisting of:
(S)-(5-chloro-2-(pyrimidin-2-yl)phenyl)(5-(((5-chloropyridin-2-yl)amino)methyl)-6-azaspiro[2.5]octan-6-yl) methanone (compound 1);
(S)-(5-(((5-chloropyridin-2-yl)amino)methyl)-6-azaspiro[2.5]octan-6-yl)(5-methyl-2-(pyridin-2-yl)phenyl)methanone (compound 2);
(S)-(5-(((5-chloropyridin-2-yl)amino)methyl)-6-azaspiro[2.5]octan-6-yl)(5-fluoro-2-(pyridin-2-yl)phenyl)methanone (compound 3);
(S)-(5-(((5-chloropyridin-2-yl)amino)methyl)-6-azaspiro[2.5]octan-6-yl)(5-fluoro-2-(2H-1,2,3-triazol-2-yl)phenyl)methanone (compound 4);
(S)-(5-methyl-2-(2H-1,2,3-triazol-2-yl)phenyl)(5-(((5-(trifluoromethyl)pyridin-2-yl)amino)methyl)-6-azaspiro[2.5]octan-6-yl)methanone (compound 5);
(S)(5-((5-chloropyridin-2-ylamino)methyl)-6-azaspiro[2.5]octan-6-yl)(5-methyl-2-(2H-1,2,3-triazol-2-yl)phenyl)methanone (compound 6);
(S)-(5-methyl-2-(pyrimidin-2-yl)phenyl)(5-(((5-(trifluoromethyl)pyridin-2-yl)amino)methyl)-6-azaspiro[2.5]octan-6-yl)methanone (compound 7);
(S)-(5-(((5-chloropyridin-2-yl)amino)methyl)-6-azaspiro[2.5]octan-6-yl)(5-methyl-2-(pyrimidin-2-yl)phenyl) methanone (compound 8); and
(S)-(5-(((5-chloropyridin-2-yl)amino)methyl)-6-azaspiro[2.5]octan-6-yl)(5-fluoro-2-(pyrimidin-2-yl)phenyl) methanone (compound 9).

A further aspect of this invention concerns a novel compound of formula (II):

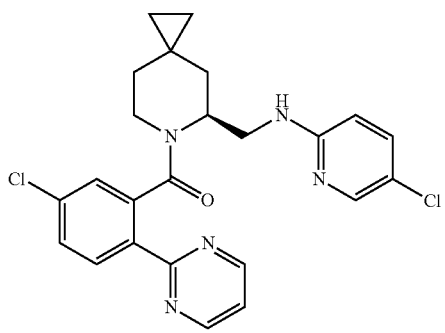

(II)

or a pharmaceutically acceptable salt thereof.

In another aspect the invention concerns a pharmaceutical composition comprising a compound of Formula (II) and a pharmaceutically acceptable carrier. In a still further aspect the invention concerns a compound of Formula (II) as medicament, in particular it concerns the compound of Formula (II) or a pharmaceutically acceptable salt thereof for use in the treatment of pathologies which require an antagonist of the NK1 receptor.

The compound of Formula (II) as such or a pharmaceutically acceptable salt thereof can be used in medicine, in particular as antagonist of the NK1 receptor. It can be used in combination with an pharmaceutically acceptable carrier and, optionally, with suitable excipients, to obtain pharmaceutical compositions. The term "pharmaceutically acceptable carrier" means solvents, carrier agents, diluting agents and the like which are used in the administration of compounds of the invention. Such pharmaceutical compositions can be administered by parenteral, oral, buccal, sublingual, nasal, rectal, topical or transdermal administration. Compositions of this invention comprising a compound of Formula (II) suitable for the oral administration will be conveniently discrete units such as tablets, capsules, cachet, powders or pellets, or as liquid suspension. The tablets can contain also suitable excipients routinely used in pharmaceutical field such as pre-gelatinised starch, microcrystalline cellulose, sodium glycolate starch, talc, lactose, magnesium stearate, sucrose, stearic acid, mannitol. Compositions for parenteral administration conveniently include sterile preparations.

Compositions for topical administration comprising a compound of Formula (II) may conveniently be formulated as creams, pastes, oils, ointments, emulsions, foams, gels, drops, spray solutions and transdermal patches.

The compounds of Formula (I) or (II) can be used in the treatment of pathologies which require the use of an antagonist of the NK1 receptor.

Compounds of Formula (I) or Formula (II) or pharmaceutically acceptable salts thereof may be of use in the treatment of the following disorders:

Depression and mood disorders, eating disorders such as Anorexia Nervosa Bulimia Nervosa; Binge Eating Disorder; sexual dysfunctions including Sexual Desire Disorders; inflammatory disorders such as asthma, influenza, chronic bronchitis and rheumatoid arthritis; allergic diseases comprise allergic disorders of the skin such as urticaria, and allergic disorders of the airways such as rhinitis; emesis, i.e. nausea, retching and vomiting (for example, emesis may be induced by drugs such as cancer chemotherapeutic agents); gastrointestinal disorders as irritable bowel syndrome, gastro-oesophageal reflux disease (GERD); skin disorders such as psoriasis, pruritis and sunburn; pain (the term "pain" includes: chronic inflammatory pain; musculoskeletal pain; lower back and neck pain; neuropathic pain; sympathetically maintained pain; myositis; pain associated with cancer and fibromyalgia; pain associated with migraine; pain associated with cluster and chronic daily headache; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; dysmenorrhea; neuralgia; fibromyalgia syndrome; complex regional pain syndrome (CRPS types I and II); neuropathic pain syndromes (including diabetic neuropathy; chemoterapeutically induced neuropathic pain; sciatica; non-specific lower back pain; multiple sclerosis pain; HIV-related neuropathy; post-herpetic neuralgia; trigeminal neuralgia); and pain resulting from physical trauma, amputation, cancer, toxins or chronic inflammatory conditions).

The invention therefore provides a compound of Formula (I) or Formula (II) or a pharmaceutical acceptable salt thereof In the treatment of conditions for which antagonism of NK1 receptor is beneficial.

The invention will be now detailed by means of the following descriptions and examples relating to the preparation of the compounds in the use of the invention and to the evaluation of their activity against NK1 receptor.

In the procedure that follows, after the starting materials, reference to a description is typically provided. The starting material may not necessarily have been prepared from the description referred to. The stereochemistry of the Examples have been assigned on the assumption that the absolute configuration centers are retained.

Reagents used in the following examples were commercially available from various suppliers (for example Sigma-Aldrich, Acros or Apollo scientific) and used without further purifications. Solvents were used in dry form. Reaction in anhydrous environment were run under a positive pressure of dry $N_2$.

Microwave reactions were run on a Biotage Initiator 2.5 instrument.

Proton Nuclear Magnetic Resonance ($^1$H NMR) spectra were recorded on Bruker Avance 400 MHz instrument. Chemical shifts are reported in ppm (δ) using the residual solvent line as internal standard. Splitting patterns are designated as: s, singlet; d, doublet; t, triplet; q, quartet; m, multiplet; b, broad signal. When more than one conformer was detected the chemical shifts of the most abundant one is usually reported.

Mass spectra (MS) were run on a Ion Trap Thermo LCQ classic spectrometer, operating in positive ES(+) and negative ES(−) ionization mode.

HPLC spectra were performed using a Waters Alliance 2965 apparatus and UV-Vis detector Waters 2996. The cromatographic method (using Phenomenex Luna C18, 150*4.6, 5μ) was the following: 35 min of elution at 30° C., mobile phase composed of different acetonitrile/methanol/$KH_2PO_4$ (20 mM pH 2.5) mixtures, flow rate of 0.6 ml/min.

HPLC spectra for chiral purity determinations were performed using a Agilent 1200 apparatus and a UV detector DAD G1315D. The cromatographic method (using a Phenomenex LUX 5u cellulose-1, 250*4.6 mm) was the following: 30 min of elution at 30° C., mobile phase 90% n-hexane 10% ethanol+0.1% DEA, flow rate of 0.5 ml/min.

UPLC spectra were performed on a Waters Acquity UPLC-SQD instrument using an Acquity UPLC-BEH C18 column (1.7 μM, 50×2.1 mm).

Flash silica gel chromatography was carried out on silica gel 230-400 mesh (supplied by Merck AG Darmstadt, Germany); in a number of preparations, Biotage automatic flash chromatography systems (Sp1 and Isolera systems) were performed, using Biotage silica cartridges.

Thin layer chromatography was carried out using Merck TLC plates Kieselgel 60F-254, visualized with UV light, aqueous permanganate solution, iodine vapours.

Abbreviations Used in the Text:
DCM Dichlorometane
DMSO-d6 Dimethylsulfoxide
DIPEA Diisopropyletyl amine
EDC.HCl 1-Ethyl-3-[3-dimethylaminopropyl]carbodiimide hydrochloride
HOBT Hydroxybenzotriazole
MeOH Methanol
TEA Triethylamine
TFA Trifluoro acetic acid
T3P Propylphosphonic Anhydride
AcOH Acetic acid
ETP Petroleum ether
AcOEt Ethyl acetate Description 1

Preparation of Intermediate 1

(S)—N-(6-azaspiro[2.5]octan-5-ylmethyl)-5-chloro-pyridin-2-amine

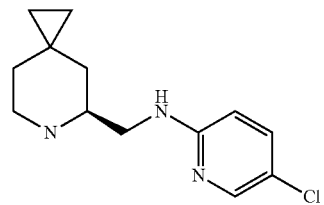 [SMILES: Clc1ccc(NC[C@@H]2CC3(CCN2)CC3)nc1]

(S)-tert-butyl 5-(((5-chloropyridin-2-yl)amino)methyl)-6-azaspiro[2.5]octane-6-carboxylate (1 eq) was dissolved in dichloromethane (10 ml/mmol) and cooled to 0° C., then trifluoroacetic acid (2 ml/mmol) was added. After 1 hour at 0° C. and 2 hours at room temperature the solution was evaporated, the residue re-dissolved in dichloromethane was washed with saturated $NaHCO_3$ aqueous solution. The organic layers were dried ($Na_2SO_4$) and concentrated under vacuum. The crude was purified by silica gel column chromatography ($CHCl_3$/MeOH=8/2) to obtain the title compound as light yellow oils with yield of 98%

1HNMR (CDCl3) δ ppm 7.94 (d, 1H) 7.32 (m, 1H) 6.48 (d, 1H) 6.22 (m, 1H) 3.74 (m, 1H) 3.37-3.50 (m, 3H) 2.95 (m, 1H) 2.25 (m, 1H) 2.08-2.66 (m, 1H) 1.23 (m, 1H) 1.07 (m, 1H) 0.41-0.55 (m, 4H).

MS ESI+m/z 254 [M+1]+

Description 2

Preparation of Intermediate 2

(S)—N-(6-azaspiro[2.5]octan-5-ylmethyl)-5-(trifluoromethyl)pyridin-2-amine

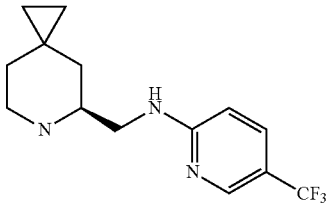 [SMILES: FC(F)(F)c1ccc(NC[C@@H]2CC3(CCN2)CC3)nc1]

(S)-tert-butyl 5-(((5-(trifluoromethyl)pyridin-2-yl)amino)methyl)-6-azaspiro[2.5]octane-6-carboxylate (1 eq) was dissolved in dichloromethane (10 ml/mmol) and cooled to 0° C., then trifluoroacetic acid (2 ml/mmol) was added. After 1 hour at 0° C. and 2 hours at room temperature the solution was evaporated, the residue re-dissolved in dichloromethane was washed with saturated $NaHCO_3$ aqueous solution. The organic layers were dried ($Na_2SO_4$) and concentrated under vacuum. The crude was purified by silica gel column chromatography (CHCl₃/MeOH=8/2 to obtain the title compound as light yellow oils with yield of 90%

ESI+m/z 287 [M+1]+

Description 3

Preparation of Intermediate 3

(S)-(2-bromo-5-chlorophenyl)(5-(((5-chloropyridin-2-yl)amino)methyl)-6-azaspiro[2.5]octan-6-yl)methanone

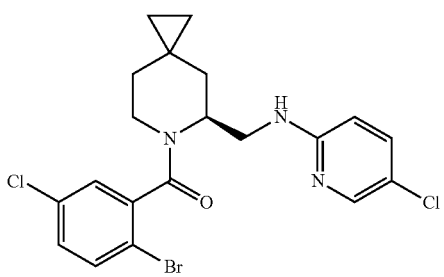 [SMILES: O=C(c1cc(Cl)ccc1Br)N1CCC2(CC2)C[C@H]1CNc1ccc(Cl)cn1]

Intermediate 1 (100 mg; 1 eq);HOBT (60 mg; 1.1 eq), EDCl. (85 mg; 1.1 eq), TEA (0.11 ml; 2 eq) and 5-chloro-2-bromo-benzoic acid (104 mg; 1.1 eq) dissolved in dichloromethane (4 ml) were stirred at 25° C. After 18 hours the mixture was poured in an aqueous HCl solution and extracted with dichloromethane. Organics were washed with saturated solution of NaHCO₃ and water, dried and evaporated to obtain 155 mg of the title compound as beige solid.

ESI+m/z 468-475

Description 4

Preparation of Intermediate 4

(S)-(5-(((5-chloropyridin-2-yl)amino)methyl)-6-azaspiro[2.5]octan-6-yl)(5-fluoro-2-iodophenyl)methanone

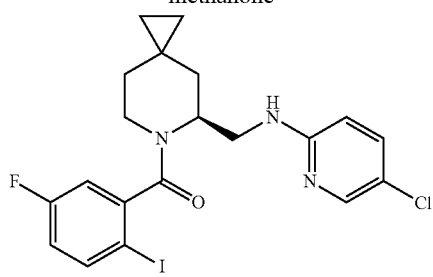

(S)-tert-butyl 5-(((5-chloropyridin-2-yl)amino)methyl)-6-azaspiro[2.5]octane-6-carboxylate (1 eq) was dissolved in dry dichloromethane (10 ml/mmol) at 0° C. with TEA (3 eq), the corresponding 2-Iodo benzoyl chloride dissolved in dry dichloromethane was added. After 2 hours the mixture was poured in aqueous NaHCO₃ and extracted with dichloromethane. The organic layers were combined, dried (Na₂SO₄) and concentrated under vacuum; crude product was purified by silica gel column chromatography (Hexane/AcOEt 9/1) to obtain the title compound with yield of 98%.

1HNMR (CDCl3) δ ppm 8.04-8.06 (m, 1H), 7.69-7.85 (m, 1H), 7.32-7.41 (m, 1H), 6.70-7.01 (m, 2H), 6.23-6.47 (m, 1H), 5.19 (m, 1H), 4.41-4.93 (m, 1H), 3.79-4.12 (m, 1H), 3.03-3.65 (m, 3H), 2.23-2.38 (m, 1H), 1.85-1.92 (m, 1H), 1.07-1.28 (m, 1H), 0.80-1.02 (m, 1H), 0.34-0.61 (m, 4H)

ESI+m/z 500 [M+1]+

Example 1

Preparation of Compound 1

(S)-(5-chloro-2-(pyrimidin-2-yl)phenyl)(5-(((5-chloropyridin-2-yl)amino)methyl)-6-azaspiro[2.5]octan-6-yl)methanone

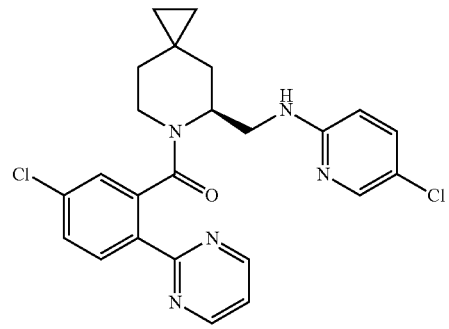 [SMILES: O=C(c1cc(Cl)ccc1-c1ncccn1)N1CCC2(CC2)C[C@H]1CNc1ccc(Cl)cn1]

Intermediate 3 (75 mg; 1 eq) was dissolved in dry DMF (2 ml), then CsF (49 mg; 2 eq), CuI (6 mg; 0.2 eq), [Ph₃P]₄Pd (19 mg; 0.1 eq) and 2-pyrimidyltributylstannane (90 mg; 1.5 eq; prepared according to *Eur. J. Org. Chem.* 2003, 1711-1721) were added. The mixture was warmed at 130° C. for 25 minutes (microwave), then poured in aqueous saturated solution of NH₄Cl and extracted with DCM. The organic layers were combined, washed with water, dried (Na₂SO₄) and concentrated under vacuum; crude product was purified by silica gel column chromatography (Cyclohexane/AcOEt 9/1 to AcOEt) then by SCX cartridge (5 g) to obtain 13 mg of the title compound.

MS (ESI) m/z 468-470;

¹HNMR (CDCl₃) δ ppm 8.80-8.94 (m, 1H), 8.66 (d, 1H), 8.22-8.43 (m, 1H), 7.86-8.07 (m, 1H), 7.12-7.52 (m, 4H), 6.22-6.74 (m, 1H), 4.98-5.22 (m, 1H), 4.32-4.81 (m, 1H), 3.08-3.97 (m, 4H), 1.90-2.40 (m, 2H), 0.65-1.65 (m, 2H), 0.15-0.65 (m, 4H)

Example 2

Preparation of Compound 2

(S)-(5-(((5-chloropyridin-2-yl)amino)methyl)-6-azaspiro[2.5]octan-6-yl)(5-methyl-2-(pyridin-2-yl)phenyl)methanone

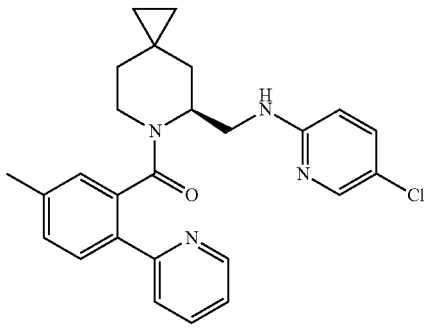 [SMILES: Cc1ccc(-c2ccccn2)c(C(=O)N2CCC3(CC3)C[C@H]2CNc2ccc(Cl)cn2)c1]

5-methyl-2-(pyridin-2-yl)benzoic acid (1 eq; prepared according to WO 2008147518), HOBT (1 eq) and EDCl.HCl (1.5 eq) dissolved in dichloromethane (5 ml/mmol) were stirred at 25° C. for 0.5-2 hours, then intermediate 1 (1 eq) dissolved in dichloromethane was added. After 18 hours the mixture was poured in an aqueous saturated solution of NaHCO₃ and extracted with dichloromethane. The crude was purified by silica gel column chromatography (DCM to DCM/MeOH=9/1) to obtain the title compound with yield of 76%.

1HNMR (CDCl3) δ ppm 8.65-8.70 (m, 1H), 8.03-8.40 (m, 1H), 6.99-7.82 (m, 6H), 6.50.6.75 (m, 1H), 6.02-6.23 (m, 1H), 5.05 (m, 1H), 4.2-4.75 (m, 1H), 3.50-3.85 (m, 2H), 2.85-3.20 (m, 1H), 1.50-2.10 (m, 2H) 1.50-2.35 (m, 2H), 0.76-1.15 (m, 2H), 0.05-0.65 (m, 4H)

MS=ESI+m/z 447 [M+H]+

Example 3

Preparation of Compound 3

(S)-(5-(((5-chloropyridin-2-yl)amino)methyl)-6-azaspiro[2.5]octan-6-yl)(5-fluoro-2-(pyridin-2-yl)phenyl)methanone

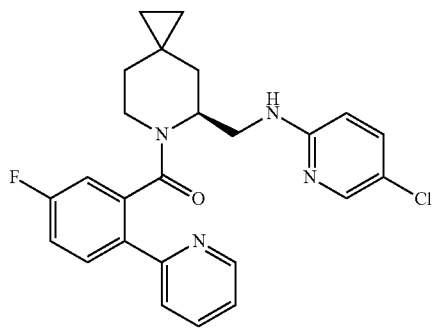 [SMILES: O=C(c1cc(F)ccc1-c1ccccn1)N1CCC2(CC2)C[C@H]1CNc1ccc(Cl)cn1]

5-fluoro-2-(pyridin-2-yl)benzoic acid (1 eq; prepared according to WO 2008147518), HOBT (1 eq) and EDCl.HCl (1.5 eq) dissolved in dichloromethane (5 ml/mmol) were stirred at 25° C. for 0.5-2 hours, then intermediate 1 (1 eq) dissolved in dichloromethane was added. After 18 hours the mixture was poured in an aqueous saturated solution of NaHCO₃ and extracted with dichloromethane. The crude was purified by silica gel column chromatography (DCM to DCM/MeOH=9/1) to obtain the title compound with yield of 54%.

1HNMR (CDCl3) δ ppm 8.70 (m, 1H), 8.03-8.41 (m, 1H), 7.66-7.93 (m, 3H), 7.05-7.40 (m, 3H), 6.46-6.83 (m, 1H), 6.01-6.21 (m, 1H), 5.05 (m, 1H), 4.20-4.70 (m, 2H), 3.48-3.81 (m, 2H), 2.90-3.30 (m, 2H) 1.50-2.35 (m, 2H), 0.76-1.20 (m, 2H), 0.05-0.60 (m, 4H)

MS=ESI+m/z 451 [M+H]+

Example 4

Preparation of Compound 4

(S)-(5-(((5-chloropyridin-2-yl)amino)methyl)-6-azaspiro[2.5]octan-6-yl)(5-fluoro-2-(2H-1,2,3-triazol-2-yl)phenyl)methanone

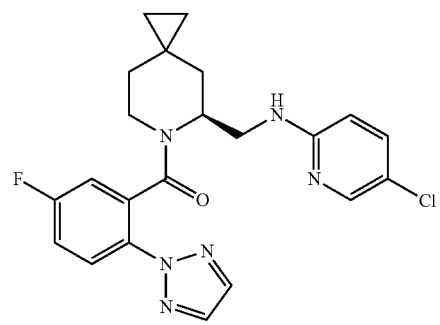 [SMILES: O=C(c1cc(F)ccc1-n1nccn1)N1CCC2(CC2)C[C@H]1CNc1ccc(Cl)cn1]

5-fluoro-2-(2H-1,2,3-triazol-2-yl)benzoic acid (1 eq; prepared according to WO 2008147518), HOBT (1 eq) and EDCl.HCl (1.5 eq) dissolved in dichloromethane (5 ml/mmol) were stirred at 25° C. for 0.5-2 hours, then intermediate 1 (1 eq) dissolved in dichloromethane was added. After 18 hours the mixture was poured in an aqueous saturated solution of NaHCO₃ and extracted with dichloromethane. The crude was purified by silica gel column chromatography (DCM to DCM/MeOH=9/1) to obtain the title compound with yield of 56%.

1HNMR (CDCl3) δ ppm 8.05-8.07 (m, 1H), 7.70-7.93 (m, 3H), 7.39-7.41 (m, 1H), 7.08-7.25 (m, 2H), 6.53 (m, 1H), 5.10 (m, 1H), 3.75-3.89 (m, 2H), 3.08-3.40 (m, 2H), 1.90-2.28 (m, 2H), 1.05-1.45 (m, 2H) 0.15-0.65 (m, 4H).

MS=ESI+m/z 441 [M+H]+

Example 5

Preparation of Compound 5

(S)-(5-methyl-2-(2H-1,2,3-triazol-2-yl)phenyl)(5-(((5-(trifluoromethyl)pyridin-2-yl)amino)methyl)-6-azaspiro[2.5]octan-6-yl)methanone

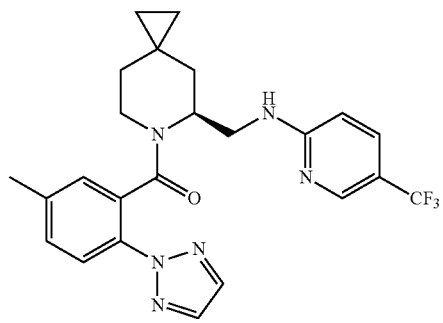 [SMILES: Cc1ccc(-n2nccn2)c(C(=O)N2CCC3(CC3)C[C@H]2CNc2ccc(C(F)(F)F)cn2)c1]

5-methyl-2-(2H-1,2,3-triazol-2-yl)benzoic acid (1 eq; prepared according to WO 2008147518), HOBT (1 eq) and EDCl.HCl (1.5 eq) dissolved in dichloromethane (5 ml/mmol) were stirred at 25° C. for 0.5-2 hours, then intermediate 2 (1 eq) dissolved in dichloromethane was added. After 18 hours the mixture was poured in an aqueous saturated solution of NaHCO₃ and extracted with dichloromethane. The crude was purified by silica gel column chromatography (DCM to DCM/MeOH=9/1) to obtain the title compound with yield of 52%.

1HNMR (CDCl3) δ ppm 8.22-8.38 (m, 1H), 7.94-8.14 (m, 1H), 7.79-7.86 (m, 1H), 7.69 (m, 1H), 7.50-7.62 (m, 1H), 7.28-7.37 (m, 1H), 7.0-7.24 (m, 1H), 6.48-6.66 (m, 1H), 5.20 (m, 1H), 4.34-4.84 (m, 1H), 3.89-4.0 (m, 1H), 3.65-3.75 (m, 1H), 3.21-3.44 (m, 2H), 3.01-3.11 (m, 1H), 2.26-2.46 (m, 3H), 1.89-2.17 (m, 1H), 1.02-1.28 (m, 1H), 0.19-0.63 (m, 4H)

MS=ESI+m/z 439 [M+H]+

Example 6

Preparation of Compound 6

(S)(5-((5-chloropyridin-2-ylamino)methyl)-6-azaspiro[2.5]octan-6-yl)(5-methyl-2-(2H-1,2,3-triazol-2-yl)phenyl)methanone

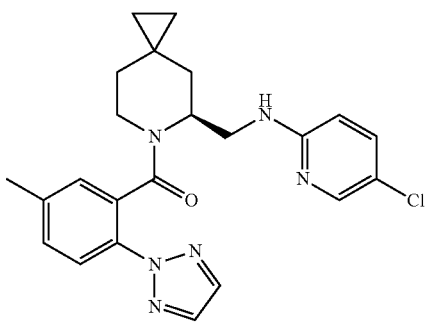 [SMILES: Cc1ccc(-n2nccn2)c(C(=O)N2CCC3(CC3)C[C@H]2CNc2ccc(Cl)cn2)c1]

To a solution of hydroxybenzotriazole (12.9 mg, 0.095 mmol) and O-(benzotriazol-1-yl)-N,N,N'N'-tetramethyluronium hexafluorophosphate HCl (23 mg, 0.12 mmol) in anhydrous dichloromethane (2 ml), 5-methyl-2-(2H-1,2,3-triazol-2-yl)benzoic acid (19.4 mg, 0.095 mmole) was added and the resulting solution was stirred for 1 h at room temperature. (±) N-(6 azaspiro[2.5]octan-5-ylmethyl)-5-chloropyridin-2-amine (Intermediate 1, 20 mg, 0.08 mmol) was added and the resulting mixture was stirred at the same temperature overnight. The mixture was washed with NaHCO₃ saturated solution (3×5 ml). After drying over Na₂SO₄ and filtration, the organic phase was evaporated under vacuum and the residue was purified by SPE-Si cartridge (2 g) eluting with a mixture DCM:MeOH (from dichloromethane to DCM:MeOH 98:2) to obtain 29 mg of the title compound.

MS (ESI); m/z 436 [MH]+

¹HNMR (CDCl₃) δ ppm 8.08-8.07 (d, 1H) 7.95-7.92 (m, 1H) 7.85-7.79 (m, 2H) 7.7 (s, 2H) 7.35-7.33 (d, 1H) 6.40-6.38 (d, 1H) 5.61-5.60 (d, 1H) 5.21-5.14 (m, 1H) 3.90-3.84 (m, 1H) 3.66-3.59 (m, 1H) 3.41-3.32 (m, 1H) 3.11-3.01 (m, 1H) 2.45 (s, 3H) 2.29-2.21 (dd, 1H) 1.99-1.85 (m, 1H) 1.19-1.16 (d, 1H) 0.75-0.68 (d, 1H) 0.58-0.27 (m, 4H)

Example 7

Preparation of Compound 7

(S)-(5-methyl-2-(pyrimidin-2-yl)phenyl)(5-(((5-(trifluoromethyl)pyridin-2-yl)amino)methyl)-6-azaspiro[2.5]octan-6-yl)methanone

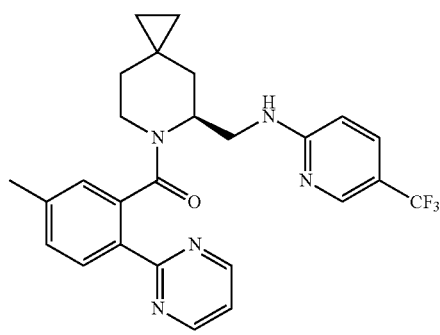 [SMILES: Cc1ccc(-c2ncccn2)c(C(=O)N2CCC3(CC3)C[C@H]2CNc2ccc(C(F)(F)F)cn2)c1]

5-methyl-2-(pyrimidin-2-yl)benzoic acid (1 eq; prepared according to WO 2008147518), intermediate 2 (1 eq) and DIPEA (2 eq) were dissolved in dichloromethane (5 ml/mmol) at 0° C., then T3P (50% in dichloromethane, 1.2 eq) was added. The mixture is stirred at reflux for 3-5 hours then at RT overnight. The reaction was washed with NaOH 1M and water, dried (Na₂SO₄) and evaporated. The crude was purified by silica gel column chromatography (DCM to DCM/MeOH=9/1) to obtain the title compound with yield of 44%.

Example 8

Preparation of Compound 8

(S)-(5-(((5-chloropyridin-2-yl)amino)methyl)-6-azaspiro[2.5]octan-6-yl)(5-methyl-2-(pyrimidin-2-yl)phenyl)methanone

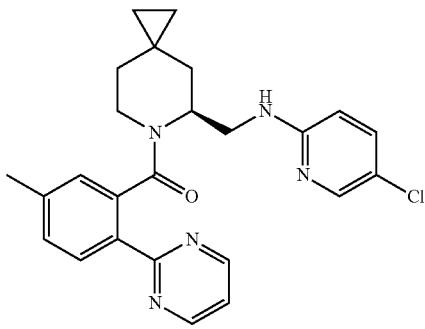 [SMILES: Cc1ccc(-c2ncccn2)c(C(=O)N2CCC3(CC3)C[C@H]2CNc2ccc(Cl)cn2)c1]

Compound 8 was obtained by the following procedure: 5-methyl-2-(pyrimidin-2-yl)benzoic acid (428 mg, 2 mmol; prepared according to WO 2008147518), intermediate 1 (500 mg, 2 mmol) and DIPEA (0.65 ml) were dissolved in DCM (5 ml) at 0° C., then T3P (50% in DCM, 1.5 g) was added. The mixture is stirred at reflux for 8 hours then at RT overnight. The reaction was washed with NaOH 1M and water, dried (Na₂SO₄) and evaporated. The crude was purified by silica gel column chromatography (DCM to DCM/MeOH=95/05) to obtain 180 mg of the title compound.

MS (ESI); m/z 446 [MH]+

$^1$HNMR (CDCl$_3$) δ ppm 8.80-8.77 (m, 1H) 8.64-8.6 (d, 1H) 8.36-8.31 (d, 1H) 8.08-8.04 (m, 1H) 7.43-7.17 (m, 3H) 7.08-7.03 (t, 1H) 6.36-6.31 (d, 1H) 5.79 (bs, 1H) 5.19-5.11 (m, 1H) 4.00-3.89 (m, 1H) 3.71-3.62 (m, 1H) 3.50-3.39 (m, 1H) 3.37-3.21 (m, 1H) 2.45 (s, 3H) 2.31-2.24 (dd, 1H) 1.99-1.88 (dt, 1H) 1.25-1.19 (d, 1H) 0.75-0.68 (d, 1H) 0.60-0.13 (m, 4H).

Example 9

Preparation of Compound 9

(S)-(5-(((5-chloropyridin-2-yl)amino)methyl)-6-azaspiro[2.5]octan-6-yl)(5-fluoro-2-(pyrimidin-2-yl)phenyl)methanone

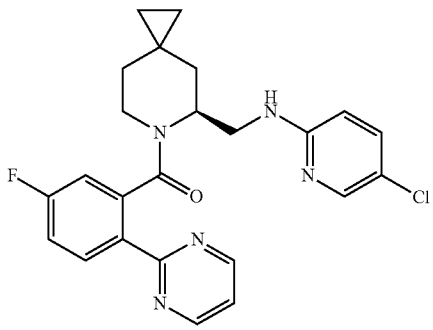 [SMILES: O=C(c1cc(F)ccc1-c1ncccn1)N1CCC2(CC2)C[C@H]1CNc1ccc(Cl)cn1]

Intermediates 4 (1 eq) was dissolved dry DMF (20 ml/mmol), then CsF (2 eq), CuI (0.2 eq), [Ph$_3$P]$_4$Pd (0.1 eq) and 2-(tributylstannyl)pyrimidine (1.5 eq; prepared according to *Eur. J. Org. Chem.* 2003, 1711-1721) was added. The mixture was warmed at 130° C. for 10 minutes (microwave), then poured in aqueous saturated solution of NH$_4$Cl and extracted with AcOEt. The organic layers were combined, dried (Na$_2$SO$_4$) and concentrated under vacuum; crude product was purified by silica gel column chromatography (DCM to DCM/MeOH 9/1) to obtain the title compound with yield of 15%.

1HNMR (CDCl3) δ ppm 8.80-8.93 (m, 1H), 8.64 (d, 1H), 8.24-8.50 (m, 1H), 7.83-8.08 (m, 1H), 6.89-7.40 (m, 4H), 6.17-6.56 (m, 1H), 5.11-5.25 (m, 1H), 4.3-4.9 (m, 1H), 3.6-4.0 (m, 2H), 3.01-3.47 (m, 2H), 1.92-2.38 (m, 1H), 1.45-1.8 (m, 1H), 0.65-1.12 (m, 1H), 0.17-0.59 (m, 4H).

ESI+m/z 474 [M+Na]+

Example 10

Evaluation of the Effects of the Invention Compounds

The utility of compounds according to the present invention as antagonists of the NK1 receptor has been determined by methodologies well known to those skilled in the art.

Evaluation of the antagonist activity of compounds at the human NK1 receptor endogenously expressed in U373 cells was determined by measuring their effect on agonist-induced cytosolic Ca2+ ion mobilization using a fluorimetric detection method.

The cells were suspended in DMEM buffer (Invitrogen), then distributed in microplates at a density of 1.10$^4$ cells/well. The fluorescent probe (Fluo4 NW, Invitrogen) mixed with probenicid in HBSS buffer (Invitrogen) complemented with 20 mM Hepes (Invitrogen) (pH 7.4) was then added into each well and equilibrated with the cells for 60 min at 37° C. then 15 min at 22° C. Thereafter, the assay plates were positioned in a microplate reader (CellLux, PerkinElmer) which was used for the addition of the test compound, reference antagonist or HBSS buffer then 5 min later 3 nM [Sar9,Met(O2)11]-SP or HBSS buffer (basal control), and the measurements of changes in fluorescence intensity which varies proportionally to the free cytosolic Ca2+ ion concentration.

The compounds, dissolved in DMSO and diluted in the medium, have been analysed in the 1 nM-1 µM concentration range (every concentration in duplicate). The antagonistic activity vs receptor NK1 of invention compounds has been expressed as pKb (co-logarithm of the apparent dissociation constant calculated by using the modified Cheng Prusoff equation) or alternatively as a percent of inhibition of the control response to 3 nM [Sar$^9$,Met(O$_2$)$^{11}$]-SP at a compound concentration of 10 µM.

The standard reference antagonist was L 733,060, which was tested in each experiment at several concentrations to generate a concentration-response curve from which its IC$_{50}$ value is calculated.

Bibliographic reference: EISTETTER, H. R., MILLS, A., BREWSTER, R., ALOUANI, S., RAMBOSSON, C. and KAWASHIMA, E. (1992), Functional characterization of neurokinin-1 receptor on human U373MG astrocytoma cells, Glia, 6: 89.

Compounds of the following example tested according to this example gave results as follows:

| Compound | pKb NK1 | NK1 % inh @10 µM |
|---|---|---|
| 1 | 8.6 | |
| 2 | | 87 |
| 3 | | 65 |
| 4 | | 61 |
| 5 | | 67 |
| 6 | | 61 |
| 7 | | 87 |
| 8 | 8.3 | |
| 9 | 8.6 | |

As shown in the table, compounds of the invention resulted surprisingly active against the NK1 receptor.

Particularly compound 1 showed a potent functional antagonism at the h-NK1 receptor with a pKb=8.6.

The invention claimed is:

1. A method of an antagonistic inhibition of NK1 receptor, said method comprising the step of administering a spiro-amino compound of Formula (I):

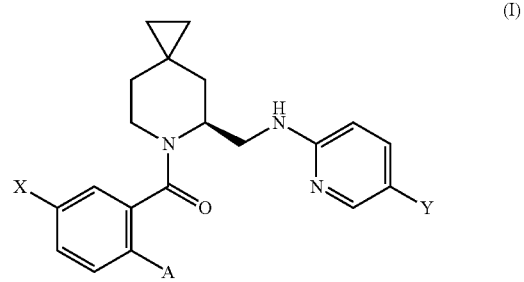

wherein

A is selected from a 5- or 6-membered aromatic ring and a 5- or 6-membered heteroaromatic ring containing 1 to 3 nitrogen atom, X is a substituent selected from the group consisting of ($C_1$-$C_3$)alkyl and halogen, Y is a substituent selected from the group consisting of halogen and trifluoromethyl or a pharmaceutically acceptable salt thereof.

2. The method according to claim 1, wherein A of the spiro-amino compound of Formula (I) is selected from the group consisting of pyrimidinyl, pyridinyl and triazolyl, more preferably pyrimidinil.

3. The method according to claim 1, wherein X of the spiro-amino compound of Formula (I) is chloro, fluoro or methyl.

4. The method according to claim 1, wherein Y of the spiro-amino compound of Formula (I) is chloro or trifluoromethyl.

5. The method according to claim 1, wherein the Spiro amino compound is selected from the group consisting of:
- (S)-(5-chloro-2-(pyrimidin-2-yl)phenyl)(5-(((5-chloropyridin-2-yl)amino)methyl)-6-azaspiro[2.5]octan-6-yl)methanone (compound 1);
- (S)-(5-(((5-chloropyridin-2-yl)amino)methyl)-6-azaspiro[2.5]octan-6-yl)(5-methyl-2-(pyridin-2-yl)phenyl)methanone (compound 2);
- (S)-(5-(((5-chloropyridin-2-yl)amino)methyl)-6-azaspiro[2.5]octan-6-yl)(5-fluoro-2-(pyridin-2-yl)phenyl)methanone (compound 3);
- (S)-(5-(((5-chloropyridin-2-yl)amino)methyl)-6-azaspiro[2.5]octan-6-yl)(5-fluoro-2-(2H-1,2,3-triazol-2-yl)phenyl)methanone (compound 4);
- (S)-(5-methyl-2-(2H-1,2,3-triazol-2-yl)phenyl)(5-(((5-(trifluoromethyl)pyridin-2-yl)amino)methyl)-6-azaspiro[2.5]octan-6-yl)methanone (compound 5);
- (S)(5(((5-chloropyridin-2-ylamino)methyl)-6-azaspiro[2.5]octan-6-yl)(5-methyl-2-(2H-1,2,3-triazol-2-yl)phenyl)methanone (compound 6);
- (S)-(5-methyl-2-(pyrimidin-2-yl)phenyl)(5-(((5-(trifluoromethyl)pyridin-2-yl)amino)methyl)-6-azaspiro[2.5]octan-6-yl)methanone (compound 7);
- (S)-(5-(((5-chloropyridin-2-yl)amino)methyl)-6-azaspiro[2.5]octan-6-yl)(5-methyl-2-(pyrimidin-2-yl)phenyl)methanone (compound 8); and
- (S)-(5-(((5-chloropyridin-2-yl)amino)methyl)-6-azaspiro[2.5]octan-6-yl)(5-fluoro-2-(pyrimidin-2-yl)phenyl)methanone (compound 9).

6. The method according to claim 1 wherein the Spiro amino compound is (S)-(5-chloro-2-(pyrimidin-2-yl)phenyl)(5-(((5-chloropyridin-2-yl)amino)methyl)-6-azaspiro[2.5]octan-6-yl)methanone (compound 1) of Formula (II)

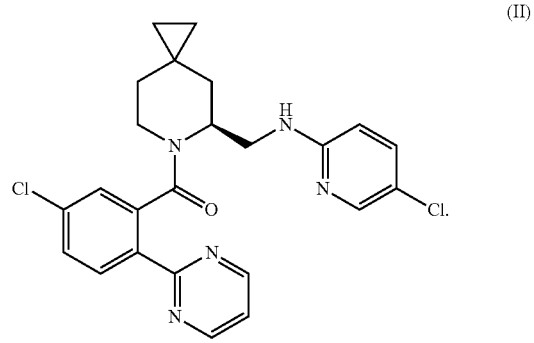 [SMILES: O=C(c1cc(Cl)ccc1-c1ncccn1)N1CCC2(CC2)C[C@H]1CNc1ccc(Cl)cn1]

* * * * *